(12) United States Patent
Nardi

(10) Patent No.: US 6,241,523 B1
(45) Date of Patent: Jun. 5, 2001

(54) RETAINER FOR DENTAL PROSTHESIS

(76) Inventor: Ezio Nardi, Via Tiazzano, 50, 40033 Casalecchio di Reno (IT)

( * ) Notice: Subject to any disclaimer, the term of this patent is extended or adjusted under 35 U.S.C. 154(b) by 0 days.

(21) Appl. No.: 09/368,526

(22) Filed: Aug. 5, 1999

(30) Foreign Application Priority Data

Sep. 23, 1998 (EP) .................................................. 98830551

(51) Int. Cl.$^7$ .................................................. A61C 13/12
(52) U.S. Cl. .................................................. 433/172
(58) Field of Search .................................... 433/172, 181, 433/182

(56) References Cited

U.S. PATENT DOCUMENTS

| | | | |
|---|---|---|---|
| 4,973,249 | * 11/1990 | Silvio et al. | 433/182 |
| 5,133,662 | * 7/1992 | Metcalfe | 433/172 |
| 5,211,561 | * 5/1993 | Graub | 433/172 |
| 5,520,540 | * 5/1996 | Nardi et al. | 433/172 |

* cited by examiner

Primary Examiner—Todd E. Manahan
(74) Attorney, Agent, or Firm—Guido Modiano; Albert Josif; Daniel O'Byrne

(57) ABSTRACT

A retainer for dental prostheses comprising a spherical male element, which is rigidly fixed to a body meant to be rigidly coupled to a corresponding implantation seat of the prosthesis, and a complementarily shaped female element, which is meant to be stably accommodated in a removable part of the prosthesis, further comprising a spherical hollow part which is complementary to the female element and is suitable to be applied to the spherical male element. The hollow part is suitable to be fixed to the male element in the correct position for coupling to the female element. The retainer further provides for a tool for fitting the hollow part and for a gauging tool which is meant to reduce the male element to size.

5 Claims, 5 Drawing Sheets

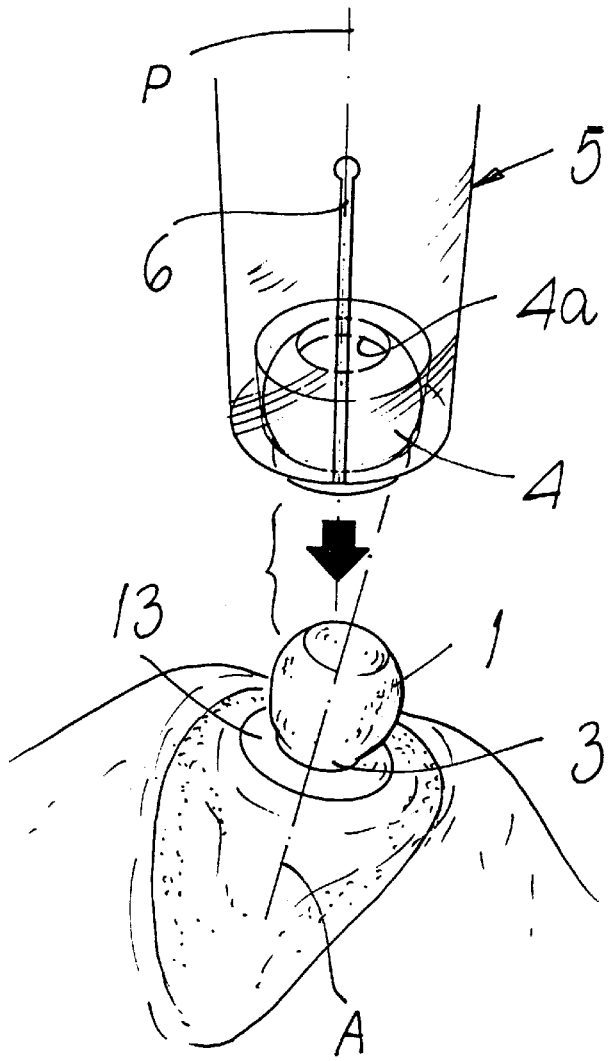
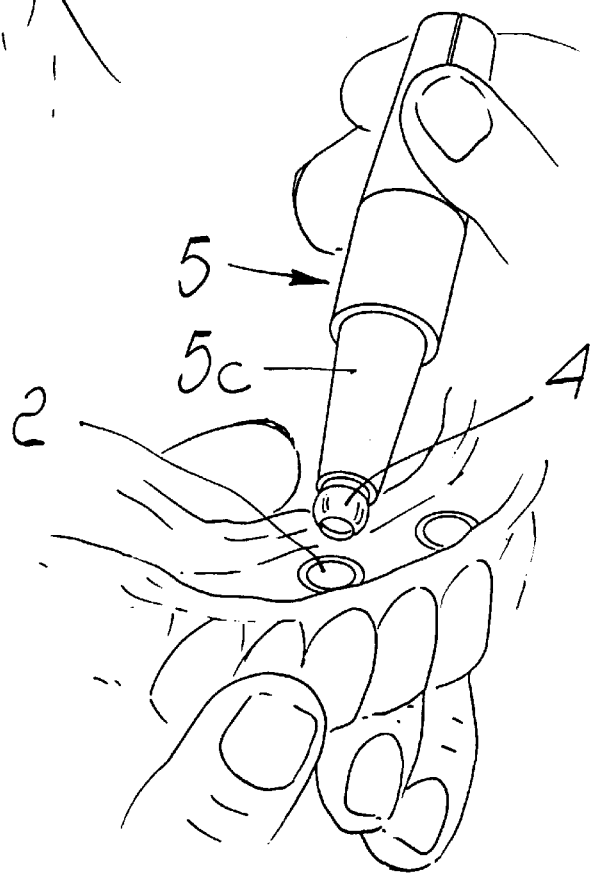
FIG.1
FIG.4

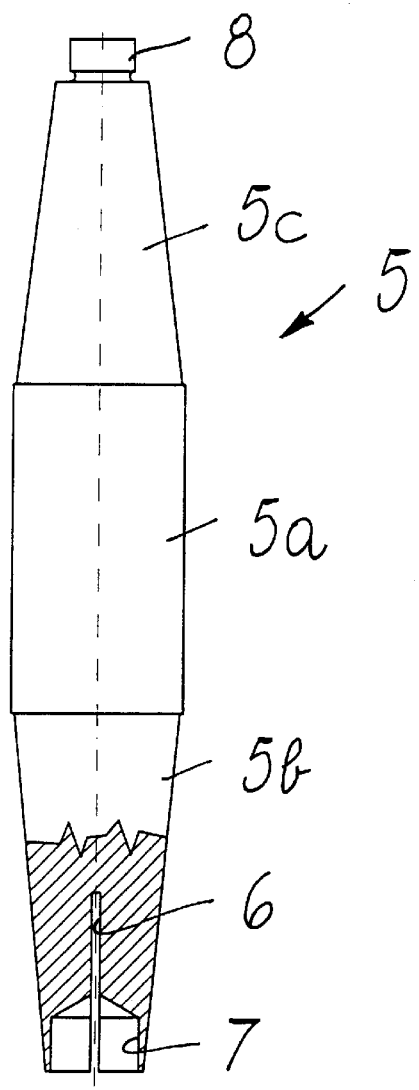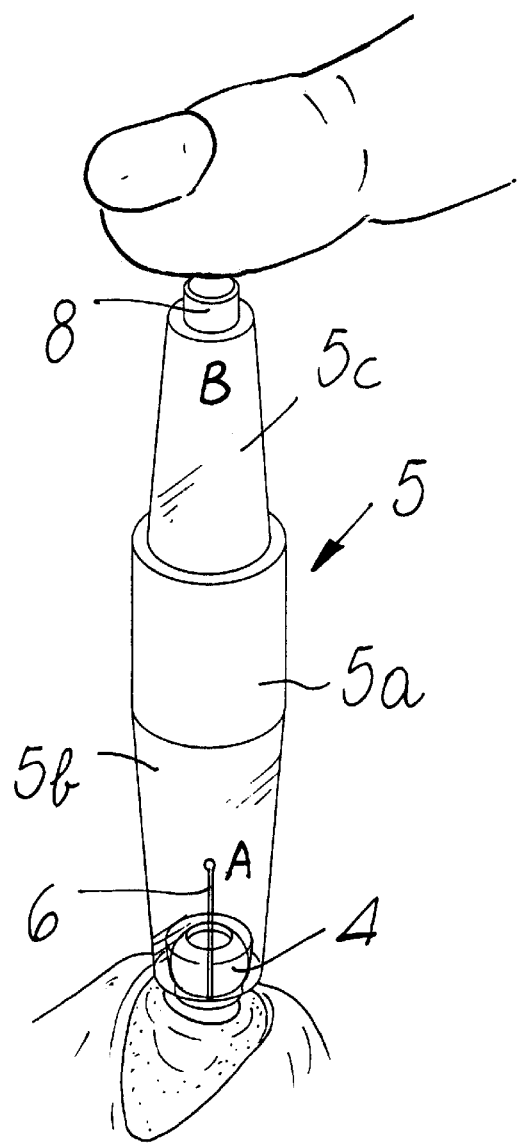
FIG. 2
FIG. 3

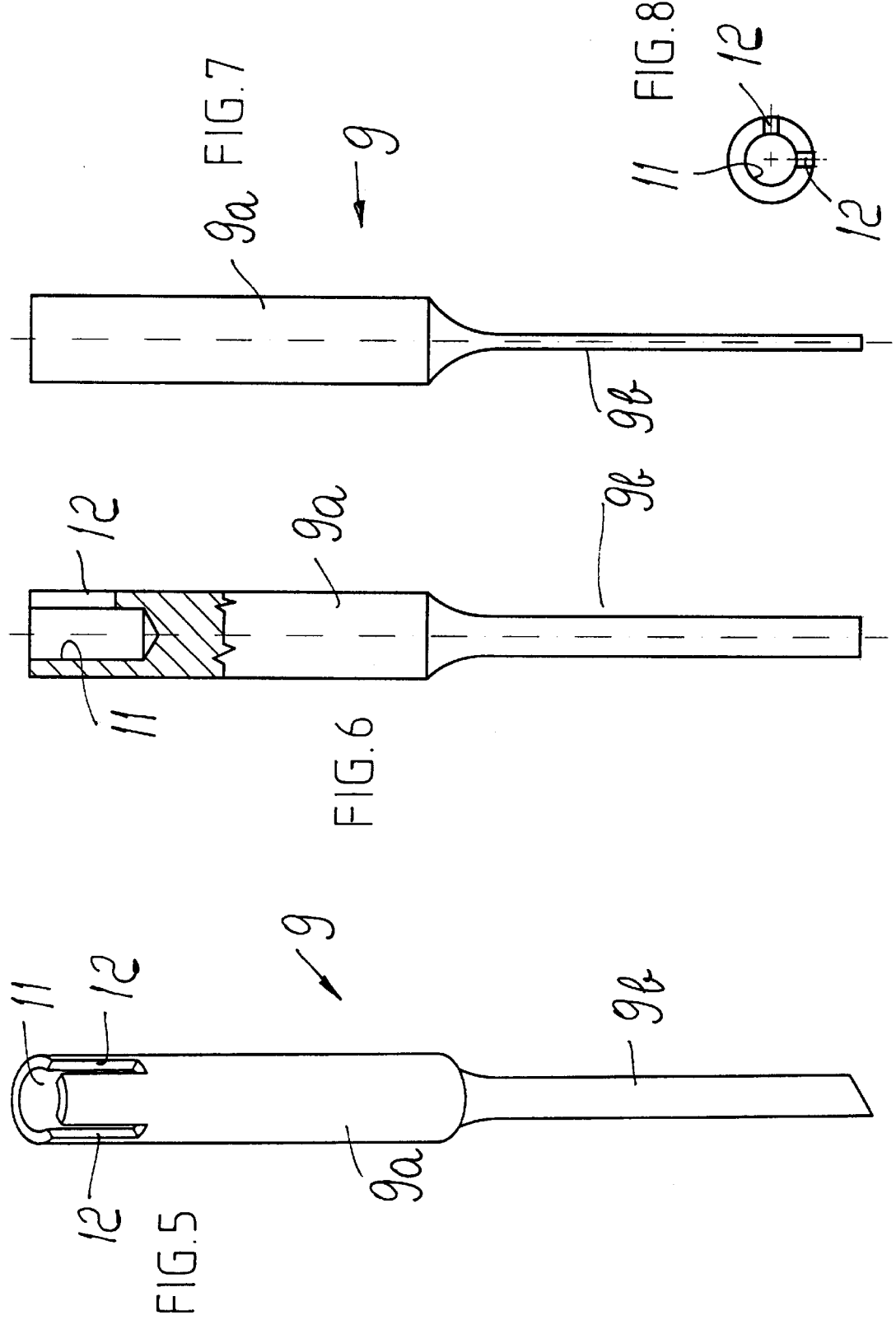

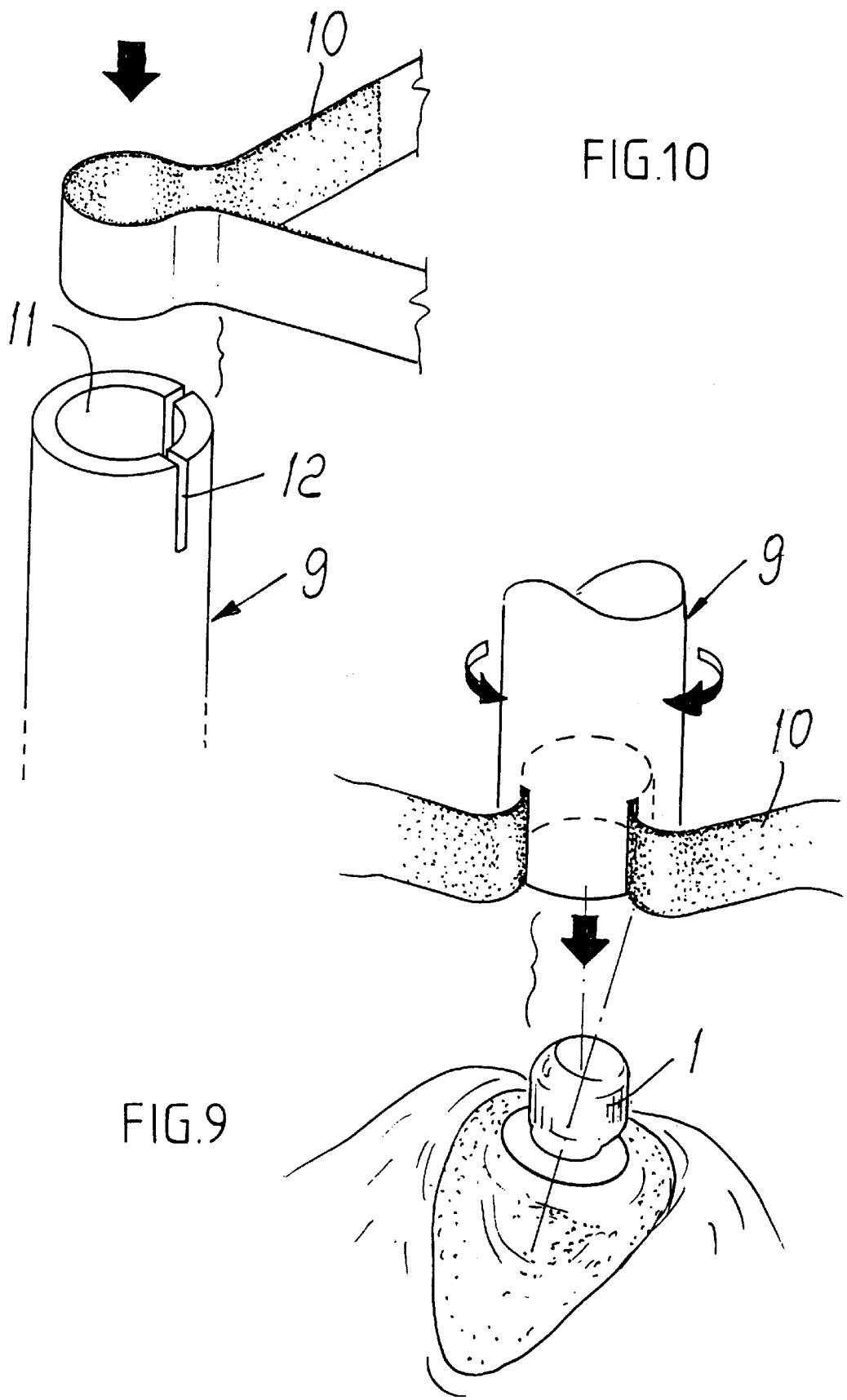

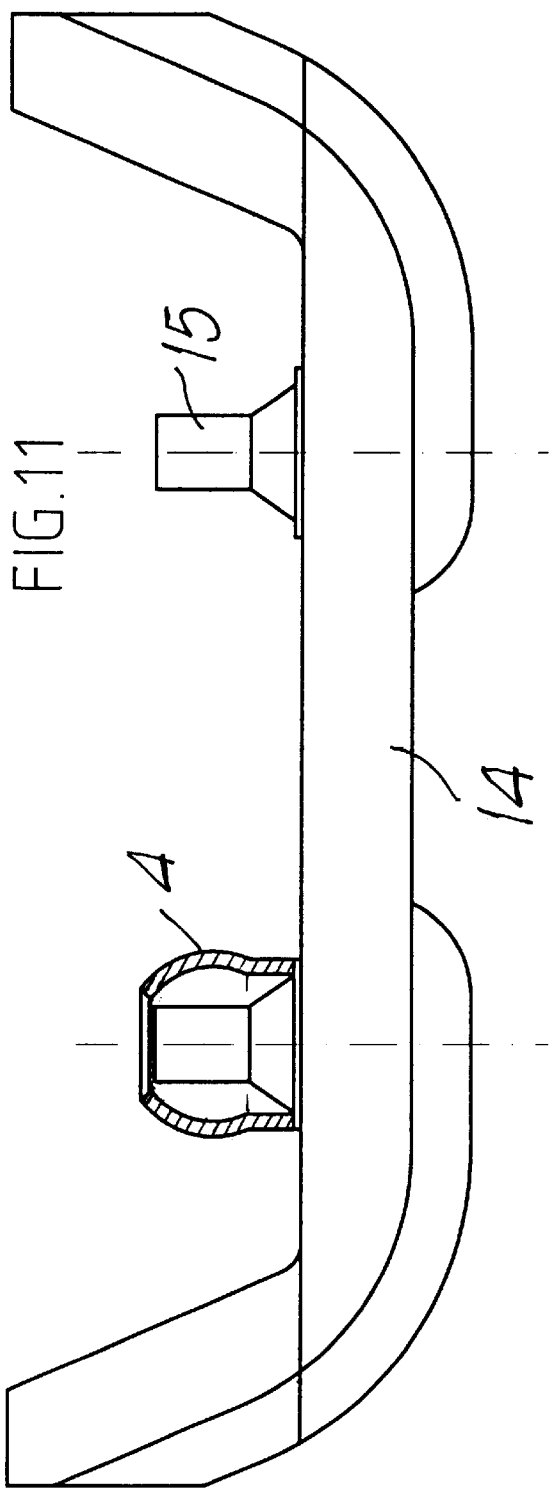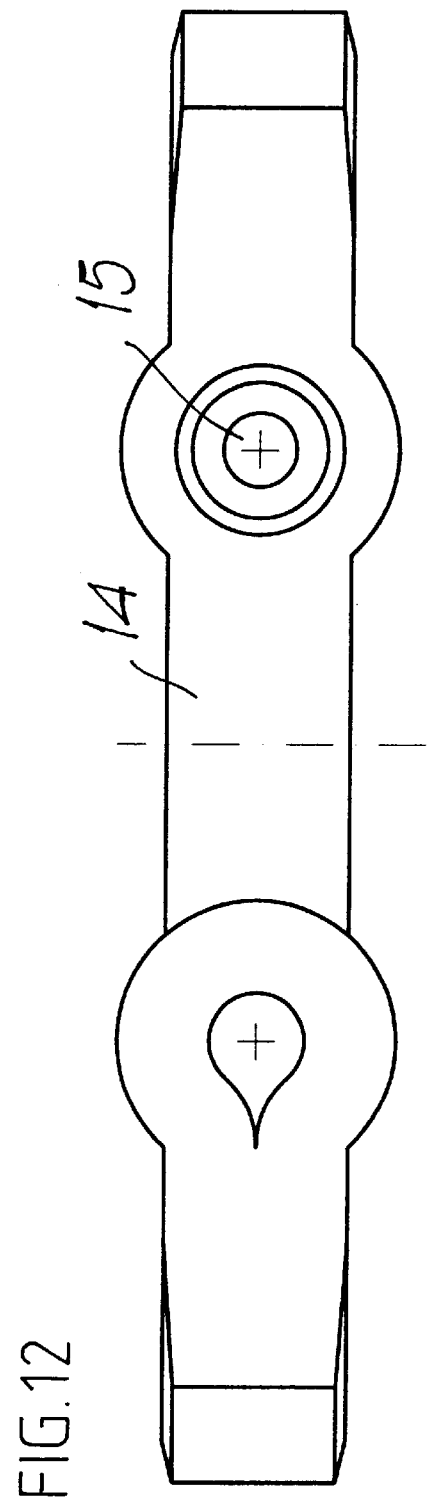

RETAINER FOR DENTAL PROSTHESIS

BACKGROUND OF THE INVENTION

The present invention relates to a retainer for dental prostheses. Removable dental prostheses are currently known which are provided with retainers that allow to anchor them to residual dental structures. In particular, retainers are known which provide for a spherical male element, which is rigidly coupled to a fixed part of the prosthesis applied in the gum region or to a crown which is fixed to a tooth, and for a complementarily shaped female element, for example a plastic cap which is meant to be stably accommodated in the removable part of the prosthesis.

The male element is formed by a body having a threaded stem which is meant to be screwed or cemented in a corresponding implantation seat of the prosthesis. The implantation seat is constituted, for example, by a substantially tubular implant which is axially provided with a threaded hole for the screwing of the stem.

One of the problems observed in the use of said retainers is constituted by the difficulty in providing a correct mutually parallel alignment of the roots or implants.

Another drawback observed in the use of the retainers is the gradual wear to which the male element is subjected. This reduces the friction of the initial coupling between the male element and the female element that is coupled thereto, severely damaging the functionality of the coupling.

SUMMARY OF THE INVENTION

The aim of the present invention is to solve the above-mentioned problem, by providing a retainer for dental prostheses which allows to provide the correct mutually parallel alignment of the roots or implants and to ensure high functionality, particularly allowing to obviate wear and the like.

Within the scope of this aim, an object of the present invention is to provide a retainer for dental prostheses which is simple in concept, very tough, safely reliable in operation and versatile in use.

This aim and this object are both achieved, according to the invention, by the present retainer for dental prostheses, comprising a spherical male element, which is rigidly fixed to a body meant to be rigidly coupled to a corresponding implantation seat of the prosthesis, and a complementarily shaped female element, which is meant to be stably accommodated in a removable part of the prosthesis, comprising a spherical hollow part which is complementary to said female element and is suitable to be applied to said spherical male element and be fixed to said male element in the correct position for coupling to said female element.

BRIEF DESCRIPTION OF THE DRAWINGS

The details of the invention will become apparent from the detailed description of a preferred embodiment of the retainer for dental prostheses, illustrated by way of non-limitative example in the accompanying drawings, wherein:

FIG. 1 is a perspective view of a retainer for dental prostheses according to the invention, during a step of the fitting of the spherical hollow part;

FIG. 2 is a partially sectional side view of a fitting tool for said hollow part;

FIG. 3 is a perspective view of another step of the fitting of the hollow part;

FIG. 4 is a perspective view of a different way of fitting the hollow part inside a cap which is included in a prosthesis;

FIG. 5 is a perspective view of a gauging device for the retainer according to the invention;

FIGS. 6, 7 and 8 are respective views of the gauging device, taken along perpendicular planes;

FIGS. 9 and 10 are partial perspective views of the gauging tool during successive steps of its use;

FIG. 11 is a side view of a bar-shaped retainer provided with the hollow part;

FIG. 12 is a corresponding plan view of the retainer, one half of the view being taken from above, the other half being taken from below.

DESCRIPTION OF THE PREFERRED EMBODIMENTS

With particular reference to the above figures, the retainer according to the invention comprises a spherical male element 1, which is rigidly coupled to a fixed part of a prosthesis applied in a gum region, and a complementarily shaped female element 2, for example a plastic cap, which is meant to be stably accommodated in the removable part of the prosthesis.

More particularly, the male element 1 is rigidly coupled to a substantially cylindrical body 3 provided with a threaded stem which is meant to be rigidly coupled to a corresponding implantation seat 13 of the prosthesis, applied in the gum region or cemented to the root of a tooth. The implantation seat 13 is constituted, in a per se known manner, by a substantially tubular implant which is axially provided with a threaded hole.

The elements of the retainer that have been described so far are preferably made of titanium.

A spherical hollow part 4, shaped complementarily to the female element 2 and preferably made of titanium and suitably turned, is suitable to be applied to the male element 1 of the retainer; in any case it is possible to provide the hollow part 4 by casting gold alloys and the like. The hollow part 4 is meant to be subsequently fixed to the male element 1, in the correct position for coupling to the female element 2, by means of a suitable cement or the like.

The spherical hollow part 4 has, at the top, a hole 4a to allow any excess of cement to exit.

In order to apply the spherical hollow part 4 to the male element 1, the retainer provides for a fitting tool 5 preferably made of transparent material.

The fitting tool 5 has a cylindrical median portion 5a from which a first frustum-shaped head 5b and a second frustum-shaped head 5c protrude axially (see FIG. 2 in particular). The first head 5b is crossed, at its end, by a slot 6 which is formed along a diametrical plane and has a front cavity 7 which is affected by the slot 6. The cavity 7 is suitable to accommodate and elastically retain the spherical hollow part 4 to be applied to the male element 1.

The second head 5c in turn has, at its end, an axial tang 8 which is meant to fit in the hollow part 4, in order to alternatively insert the hollow part 4 in the female element 2, as specified hereinafter.

The retainer further provides for a gauging device 9, made of metallic material, which is meant to reduce the male element 1 to size by means of a suitable strip 10 of abrasive material (see FIGS. 5 and 6, 7, 8). The gauging tool 9 has a cylindrical body 9a from which a laminar portion 9b protrudes axially; the cylindrical body 9a has, at its end, a gauged hole 11 provided with a pair of slots 12 formed substantially along mutually perpendicular longitudinal planes. The strip 10 of abrasive material can be inserted through the slots 12 (FIG. 9).

In practice, during use first of all the spherical hollow part 4 is inserted in the cavity 7 of the fitting tool 5 and then the hollow part 4 is fitted on the male element 1 of the retainer, which is rigidly coupled to the implantation seat provided in the gum region (FIG. 1). Then the hollow part 4 is rigidly fixed in the intended position by pressing on the fitting tool 5, as shown in FIG. 3, and using for this purpose a suitable cement or a self-polymerizing resin.

If the diameter of the male element 1 is larger than required, it is reduced by means of said gauging device 9, which is provided with the suitable strip 10 of abrasive material (FIG. 9). The gauging tool 9 is turned manually, after being fitted over the male element 1 to be reduced, so as to obtain the intended size (FIG. 10). It is then possible to insert the hollow part 4, as described above.

The fact should be noted that the spherical hollow part 4 can be fixed directly in the mouth of the patient, providing the correct mutually parallel alignment of the roots or implants. If the male element 1 has an axis A which is inclined with respect to the correct parallel alignment axis P, as shown in FIG. 1, it is in fact possible to restore the parallel alignment by fitting the hollow part 4 in alignment with the axis P.

The hollow part 4 further allows to reconstruct worn spherical male elements which have long been in the mouth of patients, restoring the original friction and grip, so as to ensure the functionality of the retainer over time.

In this case, the hollow part 4 is arranged in the cavity 7 of the fitting tool 5, as shown in FIG. 1, and an attempt is then made to fit it on the worn male element 1 in the patient's mouth; if the diameter of the male element 1 does not allow this, it is reduced by means of the gauging tool 9, provided with the strip 10 of abrasive material, as described above.

Once the size of the male element 1 that is suitable for the easy fitting of the hollow part 4 has been achieved, the hollow part 4 is extracted from the cavity 7 with the aid of the laminar portion 9b of the gauging tool 9 and is arranged on the tang 8 of said fitting tool 5, as shown in FIG. 4, which is preset for the insertion of the hollow part 4 in the female element 2 which is already fixed in the removable prosthesis. The hollow part 4 is then filled with a suitable cement by means of the laminar portion 9b, which is conveniently very small.

The prosthesis thus prepared is placed in the patient's mouth, ensuring that it is correctly positioned, and the patient is then asked to close his mouth until the cement sets. Finally, the removable prosthesis is removed, eliminating any excess.

FIGS. 11 and 12 are views of another use of the spherical hollow part 4 to strengthen retainers provided by means of materials having high biocompatibility but limited hardness, for example gold and the like. In the illustrated case, the retainer is constituted by a shaped bar 14 obtained by casting from a model made of calcinable material; the bar 14 has suitable pins 15 on which corresponding spherical hollow parts 4 are suitable to be fitted and cemented.

The retainer for dental prostheses provided with the spherical hollow part 4, with the fitting tool 5 and with the gauging tool 9 therefore achieves the aim of allowing to easily provide the mutually parallel alignment of the roots or implants, working directly in the patient's mouth, and of allowing to reconstruct worn spherical male elements, restoring the original friction and grip, so as to ensure the functionality of the retainer over time.

The spherical hollow part, made of titanium, further allows to adequately strengthen retainers made of softer materials.

It should be noted that the spherical hollow part, being very small, can be handled conveniently only by means of said fitting tool and of said gauging tool. The tools are accordingly an integral part of the retainer.

The retainer for dental prostheses thus conceived also complies with the characteristics prescribed by ISO standards related to products in this field.

Another important advantage of the proposed solution is constituted by the fact that it can be applied substantially to all currently available implants for the quick coupling of removable prostheses but also to convert retainers which have already been fixed in the patient's mouth with spheres having a larger diameter or retainers having a different shape, for example conical or cylindrical pins, so as to achieve better retention.

In the practical embodiment of the invention, the materials employed, as well as the shapes and the dimensions, may be any according to requirements.

The disclosures in European Patent Application No. 98830551.2 from which this application claims priority are incorporated herein by reference.

What is claimed is:

1. A retainer for dental prostheses, comprising a spherical male element, which is rigidly fixed to a body rigidly coupled to a corresponding implantation seat of the prosthesis, and a complementarily shaped female element, which is stably accommodated in a removable part of the prosthesis, the retainer further comprising a spherical hollow part which is complementary to and fitted inside said female element and is applied to said spherical male element and rigidly fixed to said male element by means of a fixing substance in a correct position for coupling to said female element, said spherical hollow part having a top hole for permitting exit of any excess of said fixing substance.

2. The retainer according to claim 1, wherein said fixing substance comprises a cement interposed between said male element and said spherical hollow part.

3. The retainer according to claim 1, wherein said fixing substance comprises a self-polymerizing resin interposed between said male element and said spherical hollow part.

4. The retainer according to claim 1, wherein said spherical hollow part is made of a rigid material.

5. The retainer according to claim 1, wherein said spherical hollow part is fitted and fixed, through the interposition of a cement, on a pin which protrudes from a retainer bar which is cast using biocompatible material.

* * * * *